US006586735B1

(12) United States Patent
Haking et al.

(10) Patent No.: US 6,586,735 B1
(45) Date of Patent: Jul. 1, 2003

(54) METHOD FOR DETECTING AN ELEMENT IN A SAMPLE (75) Inventors: Ansgar Haking, Eppelheim (DE); Karsten Richter, Ketsch (DE)

(73) Assignee: Deutsches Krebsforschungszentrum Stiftung des Öffentlichen Rechts, Heidelberg (DE)

( * ) Notice: Subject to any disclaimer, the term of this patent is extended or adjusted under 35 U.S.C. 154(b) by 0 days.

(21) Appl. No.: 09/476,514

(22) Filed: Jan. 3, 2000

Related U.S. Application Data (63) Continuation of application No. PCT/DE98/01865, filed on Jul. 6, 1998.

(30) Foreign Application Priority Data

Jul. 4, 1997 (DE) .......................... 197 28 698

(51) Int. Cl.[7] .......................... H01J 37/07; H01J 26/00; H01J 26/295; G21N 23/00
(52) U.S. Cl. ...................... 250/307; 280/305; 280/306; 280/310; 280/311
(58) Field of Search ................................ 250/307, 311, 250/397, 306, 305, 310; 356/336, 237

(56) References Cited

U.S. PATENT DOCUMENTS

| 3,866,044 A | * | 2/1975 | Grund ......................... 250/310 |
| 3,909,610 A | * | 9/1975 | Kokubo ....................... 250/305 |
| 5,231,287 A | * | 7/1993 | Sekine et al. ................ 250/305 |
| 5,629,865 A | * | 5/1997 | Roth ............................ 364/508 |
| 5,818,583 A | * | 10/1998 | Sevick-Muraca et al. ... 356/336 |
| 6,067,154 A | * | 5/2000 | Hossain et al. ........... 356/237.2 |

OTHER PUBLICATIONS

H. Tenailleau et al. (1992) "A New Background Substraction for Low–Energy EELS Core Edges" *The Journal of Microscopy*, 166(3):297–306.

* cited by examiner

Primary Examiner—John R. Lee
Assistant Examiner—Dav A. Vanore
(74) Attorney, Agent, or Firm—Collard & Roe, P.C.

(57) ABSTRACT

A method for detecting an element in a sample using a transmission electron microscope to measure a first image of the intensities of the sample at an energy loss in the range of the element signal. The background at various points is determined in a comparator sample which does not contain the element intensity. Energy loss is determined at the front of the element signal, and an energy loss is determined in the range of the element signal. From these values an approximation function is calculated so that an image of the pure element-specific intensities can be calculated.

10 Claims, 5 Drawing Sheets

METHOD FOR DETECTING AN ELEMENT IN A SAMPLE

This application is a continuation of PCT International Application No. PCT/DE98/01865, filed on Jul. 6, 1998.

BACKGROUND OF THE INVENTION

1. Field of the Invention

The invention relates to a procedure for the detection of an element in a sample. A transmission electronic microscope is used to measure a first image of the intensities of the sample for an energy-loss domain before the element edge. A second image of the intensities of the sample for an energy loss is measured in the area of the element edge.

2. The Prior Art

This procedure is also termed the "two-windows difference method." The difficulty of this method is that the intensity of the background is a function of the energy loss and, therefore, various background intensities need to be determined within the energy window. The background intensity essentially depends on the thickness of the sample point and decreases as energy loss increases. In order to determine the purely element-specific signal, i.e. the element-specific intensity, initially the intensity is measured in the energy-loss domain specific to the element to be detected.

Therefore, a background value in the energy-loss domain is subtracted from these measured values, where the background in the element-specific energy window is a function of the background outside the element-specific energy window. In the well known method, the assumption is made that the intensity of the background in the domain of the energy window is a linear function of the intensity before the energy window.

For many applications, this assumption is approximately justified. However, the way in which the parameters of the linear function are to be calculated is not satisfactorily described in the state of the art. Furthermore, in many cases a linear function does not correspond to the natural facts.

SUMMARY OF THE INVENTION

It is therefore an object of the invention to further develop a generic procedure so that the function described can be determined and reproduced in order to calculate a more precise image of the element-specific intensities.

The invention comprises a procedure for the detection of an element in a sample comprising the steps of measuring a first image of the intensities $I_{1p}$ of the sample for an energy loss before the element edge using a transmission electronic microscope. Then a second image of the intensities $I_{2'p}$ is measured for an energy loss in the area of the element edge. The next step is determining the non-element-specific intensities $I_1$ of the sample for an energy loss before the element edge for various points at a reference sample point that does not contain the element. Then the non-element-specific intensities $I_2$ for an energy loss are determined in the area of the element edge are determined. An approximation function $I_2(I_1)$ and an image of the element-specific intensities $I_E$ is then calculated from these values. The corresponding intensity $I_{2p}$ with the approximation function for every point in the first image with the intensity $I_{1p}$ is calculated, and the difference between the measured intensity $I_{2'p}$ and the calculated intensity $I_{2p}$ as the element-specific intensity $I_E$ for the corresponding point in the second image is determined.

In the present invention, the intensity $I_1$ for an energy loss at various points of a reference sample not containing the element is determined before the element edge. The non-element-specific intensities $I_2$ for an energy loss are determined in the area of the element edge. From these values an approximation function $I_2(I_1)$ is calculated and an image of the element-specific intensities $I_E$ is calculated. Therefore, for every point in the first image with the intensity $I_{1p}$, the corresponding intensity $I_{2p}$ is calculated from the approximation function and, for the corresponding point in the second image, the difference between the measured intensity $I_{2'p}$ and the calculated intensity $I_{2p}$ is determined as the element-specific intensity $I_E$.

The procedure of the invention allows the function $I_2(I_1)$ to be calculated experimentally. This is useful because it allows the removal of the non-element-specific background from the image of the intensities measured in the area of the element edge for an energy loss. Therefore, systematic error is markedly reduced and the background subtraction can be matched to each sample and to all variable parameters that can be set at the microscope.

The intensity pair $I_1/I_2$ can be graphically represented so that it can also be easily determined visually whether the calculated approximation function corresponds with the measured values.

It is advantageous for the reference sample to display a course of different sample thicknesses. Since sample thickness affects the background signal most strongly, a course of different sample thicknesses permits the measurement of various background signals and thus the determination of various intensity pairs $I_1/I_2$. This course should display no steps and preferably takes the shape of a ramp.

Preferably, the reference sample displays at least the thickness of the sample. This ensures that, for all background signals occurring in the area of the sample, there is a corresponding background signal to be determined from the reference sample.

Reference samples consisting of pure carbon have shown themselves to be suitable. Such reference samples can be produced without difficulty in all electron-microscope oriented laboratories and are mainly suitable for biological samples if they have not subsequently been treated with heavy metals.

A more detailed determination of the background signal may be required. The reason is that, as well as a purely mass-thickness contrast, a further contrast mechanism plays a role in the emergence of an image. It may, for example, be an inhomogeneous concentration of various elements. A contrast resulting from this is termed a "compositional contrast" (CC). For this reason, it can be advantageous for the reference sample to contain at least two elements. Because of the high carbon content in biological samples, carbon is recommended as one of the elements, while the other element should be a heavier element than carbon, e.g. nitrogen, oxygen or sulphur.

However, the preparation of suitable reference samples is difficult. In a reference sample intended to contain oxygen in addition to carbon, for example, almost all the oxygen is lost by evaporation. Furthermore, a heavier element is more suitable for a reference sample. Sulphur can be prepared in different thicknesses only with great difficulty, if at all.

For this reason, dithiouracil (DTU) was used. In DTU, both of the oxygen atoms of the uracil, which is one of the four bases of DNA, are replaced by sulphur atoms. Compounds containing oxygen may, however, also be considered.

In order to reduce noise in the graphs derived from the images, it is suggested that the intensity of each point be measured as the mean value of its environment. Each of the images, for example, can consist of 0141×1024 image points, the intensity value of each image point being replaced by the mean value of the environment of 10×10 image points. After the calculated function is obtained, however, the original images are used in further work.

In order to determine the quality of the approximation function and, where appropriate, replace the approximation function with a further approximated function, it is suggested that the quality of the function $I_2$ ($I_1$) be determined by statistical functions. This also permits the reproducible determination of error in the procedure.

The procedure of the invention was tried with great success on the element phosphorus. The procedure can also, however, be used for the detection of other elements, e.g. iron. Since DNA contains phosphorus, the procedure of the invention permits the course of DNA in, for example, viruses or other DNA protein complexes to be shown.

If a residual contrast remains after the procedure of the invention has been carried out, at least a third image of the intensities $I_{3'p}$ of the sample for a third energy loss can be recorded. This energy loss should also lie before the element edge and should differ from the energy loss of the first image. Third intensities $I_{3p}$ for the third energy loss for the various points are then determined at the reference sample point. From the determined first and third intensities $I_1$, $I_3$, the approximation function $I_2$ ($I_1$,$I_3$) is then calculated. The image of the element-specific intensities $I_E$ is calculated, in that, for each point of the first and third image, the corresponding intensity $I_2$ is calculated from the approximation function $I_2$. For the corresponding point in the second image, the difference between the measured intensity $I_{2'p}$ and the calculated intensity $I_{2p}$ is determined as the element-specific intensity $I_E$.

The carrying out of such a procedure makes it possible to detect two contrast mechanisms. To make such detection possible without difficulty, the reference sample should be made in such a way that, besides the previously described change in thickness, it also displays an overlap between the two components of the reference sample, e.g. pure carbon and DTU. This can be achieved if carbon and DTU are evaporated in sequence, a mask being displaced between the evaporation processes. The ramps of the two elements are similarly displaced, so that all mass thicknesses and concentration differences in the reference sample can be found.

Expressed in general terms, the calculation of the image of the element-specific intensity $I_E$ is given by the following formula:

$$I_E = I_{2'p} - I_{2p} = I_{2'p} - \left(a + \sum_{i=1}^{N} b_i I_1^i + \sum_{i=1}^{N} c_i I_3^i\right)$$

in which only one of the sums is used if only two images are used and correspondingly more sums are used if more images are used.

BRIEF DESCRIPTIONS OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views.

DETAILED DESCRIPTION OF THE PREFERRED EMBODIMENT

Figure 1:
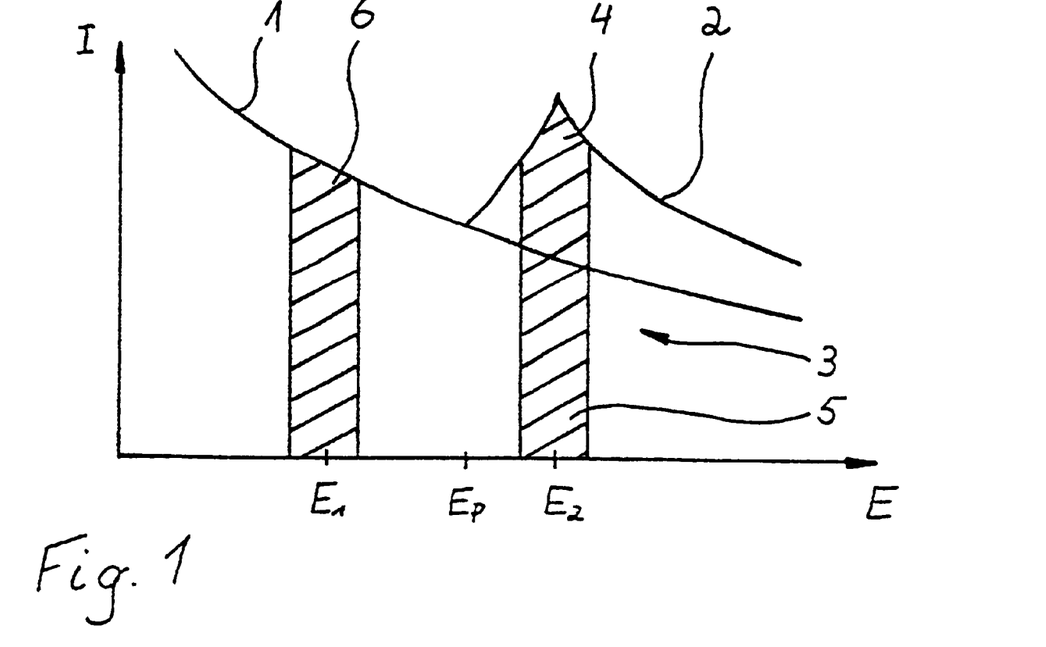
FIG. 1 shows the intensity I of the electron beam against the energy loss E at a thick sample point.
Figure 2:
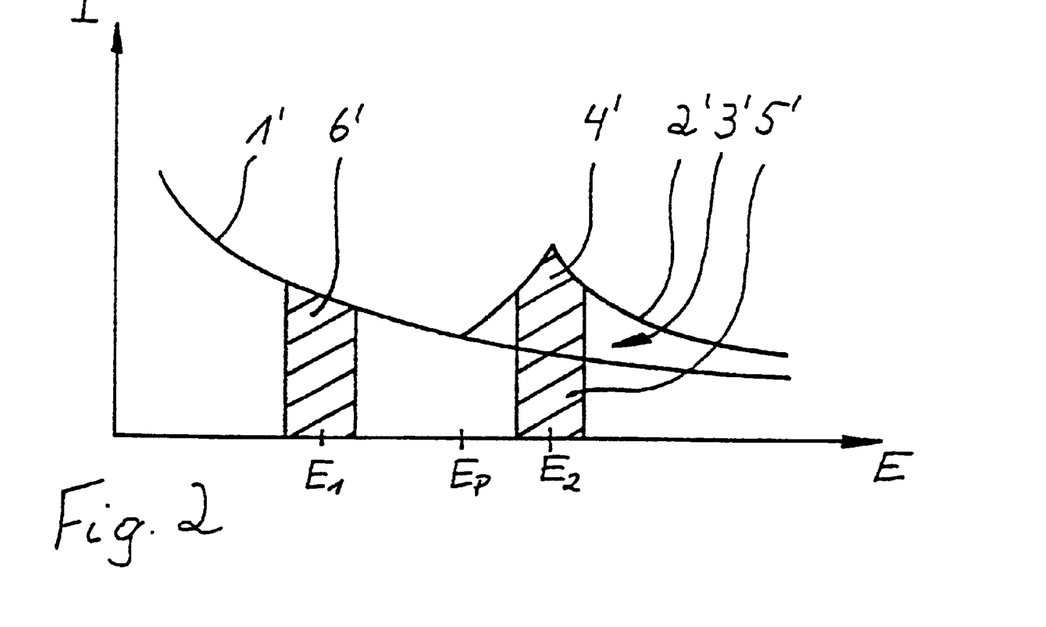
FIG. 2 shows the intensity I against the energy loss E at a thin sample point.

For each element in the periodic table there are characteristic energy-loss ranges in which the intensity of the electron beam is greater if that element is present in the sample. FIGS. 1 and 2 model the intensity of the electron beam as a function of energy loss for two different thick sample points in which the target element sought is present. In this case, the target element is phosphorus. Two different types of signal can be distinguished in both figures: a non-element-specific background 1 or 1', which decreases as energy loss increases, and an element-specific signal 2 or 2', which occurs at and above an energy level that is typical of the element. For phosphorus, this signal occurs at $E_p$=130 eV and reaches a maximum at $E_2$=160 eV. Because of the form of the element-specific signal, an "element edge" is also spoken of. The position of this element edge is specific to each element.

In the present case, the presence of phosphorus is intended to be shown and therefore the electrons that have lost 160 eV ($E_2$) are filtered out. The range around 160 eV below the element-specific signal 2 describes a surface 3 corresponding to the intensity $I_{2'p}$ of the sample for an energy loss in the area of the element edge. This intensity range 3 or 3' consists of a proportion 4 or 4' of the pure element signal and a proportion 5 or 5' of the background. In order to obtain the pure element signal 4 or 4', this background 5 or 5' must be removed by calculation. In the state of the art, this background is calculated from images before the edge using a predefined computation algorithm. Some examples of such algorithms are known as "power-law", "exponential-law" and "two-windows differential-law".

The present procedure is based on the two-windows difference method. In order to calculate the background, the intensity range 6 is initially measured before the edge for an energy loss $E_1$=115 eV. This is because the ratio between the intensity range 5 on the edge and the intensity range 6 before the edge depends not only on the layer thickness of the sample point but also on the selected energy-loss ranges.

A reference structure is initially investigated in order to determine the function relating the intensity on the edge and the intensity before the edge for specified energy losses $E_1$ before the edge and $E_2$ on the edge.

A preparation or part of the sample under investigation that is known with certainty not to contain the element to be detected serves as the reference structure or reference sample. The reference sample can thus be a part of a preparation under investigation in which the element to be detected is not present. Preferably, however, a reference structure known to have the same properties with respect to the background signal as the sample under investigation is generated on the object holder as an extra preparation, in addition to the sample under investigation. The reference structure does not contain the sought element.

For the investigation of macromolecules, the material to be investigated is mounted on a carbon foil that lies on a copper mesh. This procedure is generally established and has been modified so that at least one carbon ramp is evaporated on to the carrier foil. Only then is the material under investigation applied.

Figure 3:
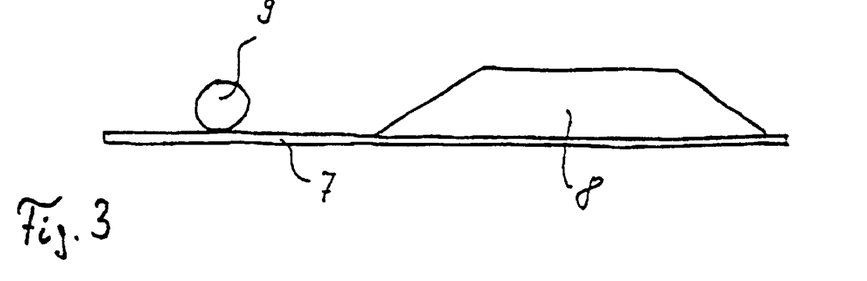
FIG. 3 shows a cross-section through a preparation with a sample and a reference sample.

FIG. 3 shows a carbon carrier foil 7 on which a carbon ramp 8 has been additionally applied as a mass-thickness marker. In addition to the carbon ramp 8, the material under investigation 9 is applied to the carrier foil. In the application of the mass-thickness marker, care is taken to ensure that a ramp and not a step results, so that the background can be determined for all thicknesses between the minimum (the carrier foil) and the maximum of the mass-thickness marker. The maximum thickness of the marker has been selected so that at least the thickness of the structure under investigation is achieved. In the present case, turnip yellow mosaic viruses (TYMV) were used as the test preparation.

FIGS. 4 and 5a, 5b and 5c show images with 1024 by 1024 image points were made of the test preparation with virus and carbon ramp. An electron beam with an energy loss $E_1=115$ eV, i.e. before the phosphorus edge, was used for the first image and an electron beam with an energy loss $E_2=160$ eV, at the maximum of the phosphorus edge, was used for the second image. In order to reduce noise in the graphs derived from the images, the intensity value of each image point was replaced by the mean value of its environment, consisting of 10×10 image points, and thereafter the original images were used in further work. An area was then selected that cound be taken not to contain any phosphorus. Within this range, the intensity of many image points was measured before and on the edge, resulting in a table of value pairs $I_1$ (before the edge) and $I_2$ (on the edge). These value pairs were graphed to show the intensity $I_2$ (on the edge) against the intensity $I_1$ (before the edge) for individual image points. In the selection of the value pairs, care was taken to ensure that the points on the graphy were uniformly distributed over the entire intensity range, giving a representation with no gaps.

Figure 4:
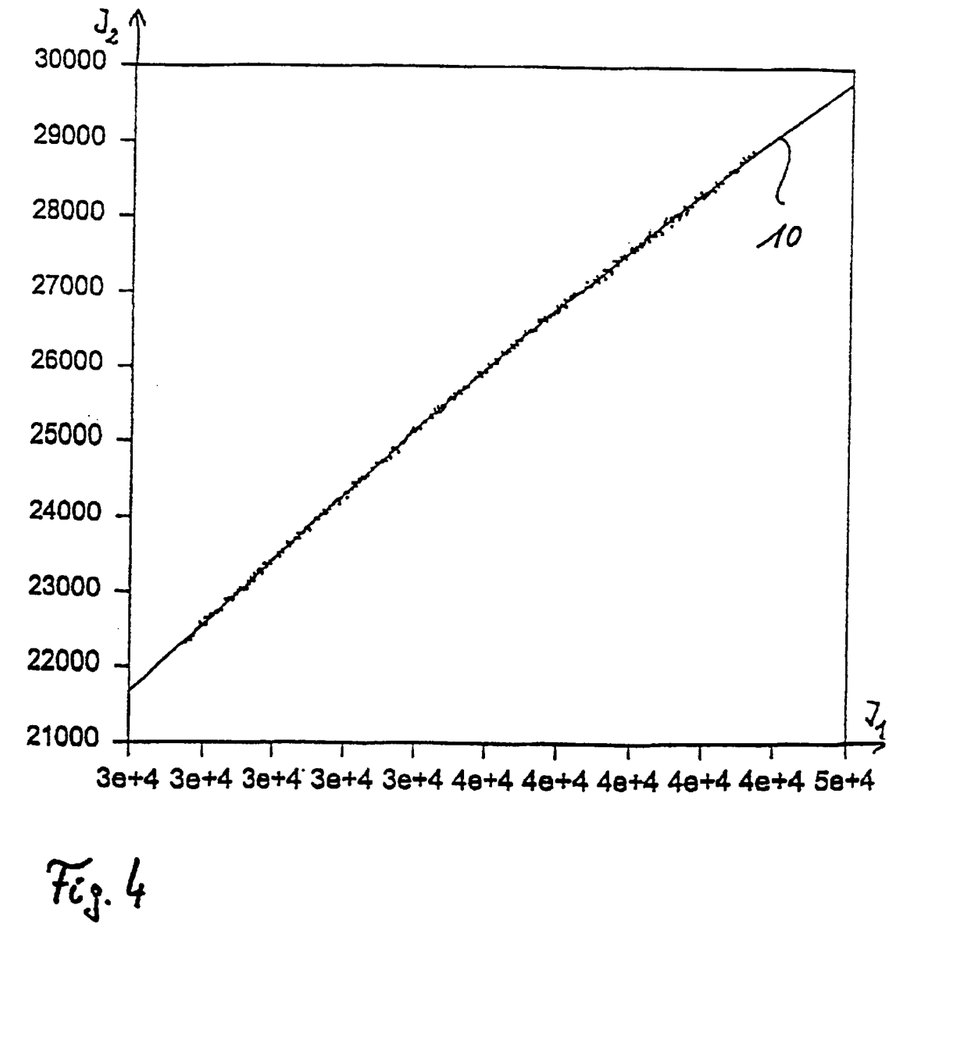
FIG. 4 shows a graphical representation of the intensity $I_2$ for an energy loss in the area of the element edge against the intensity $I_1$ for an energy loss before the element edge for various points of the reference sample.
Figure 5:
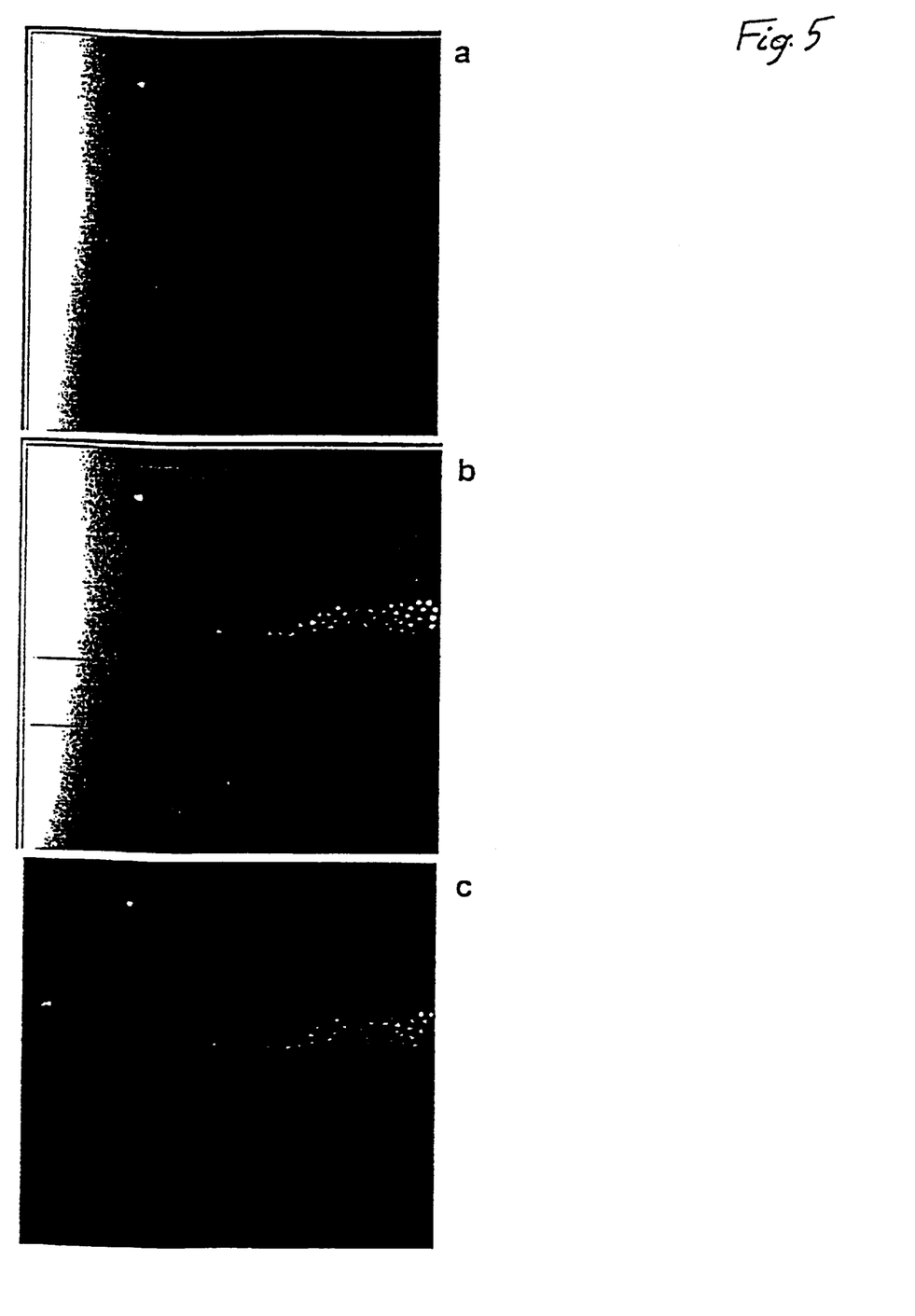
FIG. 5 shows photographs of images, one with $E_1$=115 eV, i.e. before the phosphorus edge and one with $E_2$=160 eV, at the maximum of the phosphorus edge (FIGS. 5a/b), with each of the images consisting of 1024×1024 image points.

A curve was fitted to the points. In the present case, a third-order polynomial gave a good approximation function 10. The quality of the approximation function 10 can be verified on the basis of statistical criteria. For the investigated range of the mass-thickness marker 8, this function gives a ratio of $I_2$ to $I_1$ for the non-element-specific background.

With the aid of the calculated function, the background was now subtracted from the previously generated image on the edge and from the image before the edge for an energy loss $E_1$ of 160 eV, so that only the pure energy signal remained. An image resulted that showed only the element-specific intensities $I_E$. In addition, the corresponding intensity $I_{2'p}$ was initially calculated with the approximation function for each point with the intensity $I_{1p}$ in the first image and, for the corresponding point in the second image, the difference between the measured intensity $I_{2'p}$ and the calculated intensity $I_{2p}$ was determined as the element-specific intensity $I_E$.

It turns out that, in certain samples, a marked residual contrast still remains after the making of the image generated by means of the procedure represented in FIGS. 1 to 5. This can be ascribed to the fact that, in addition to a pure mass-thickness contrast, at least one further contrast mechanism plays a role in producing the image. Such a contrast may, for example, be a "compositional contrast" (CC), which stands for an inhomogeneous concentration of different elements in a sample.

In this respect, a reference sample should be selected that contains at least two of the background elements occurring in the usual samples. Such a reference sample should, on the one hand, display the previously described ramps for each of the elements contained and, on the other hand, should also display different concentration proportions of the two elements. An example of such a reference sample is shown schematically in FIG. 6. In this connection, it is not imperative for the reference samples to be of a pure element. As shown in the specimen model described below, a compound or a mixture of elements or compounds can be used instead.

Figure 6:
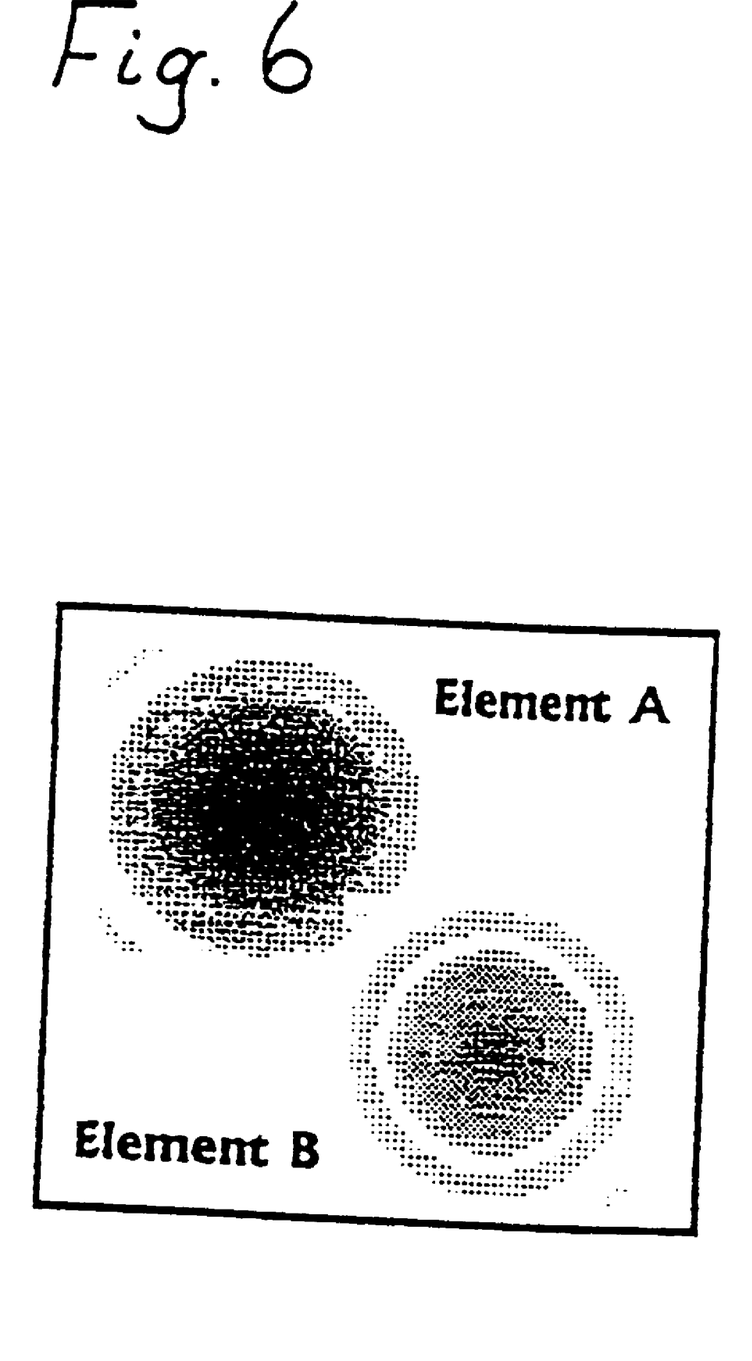
FIG. 6 shows a schematic representation of a reference sample comprising two elements.

Because of the simplicity with which it can be represented, a reference sample that contains pure carbon (as element A), and dithiouracil (DTU) (as element B), is recommended. Here the DTU, due to its composition $(H_4C_4N_2S_2)$, enables nitrogen and sulphur, as well as carbon, to be included in the background calculation. However, compounds containing oxygen, such as uracil, may alternatively be used.

Images of a reference sample made of carbon and dithiouracil, and of a section, were made at 50, 80, 115 and 150 eV (see FIGS. 7a to d). Using the reference sample, a background subtraction is to be performed as a quality check at 115 eV using the images at 50 and 80 eV. Following that, a background subtraction is performed for phosphorus detection, using the before-edge images at 80 and 115 eV.

Figure 7:
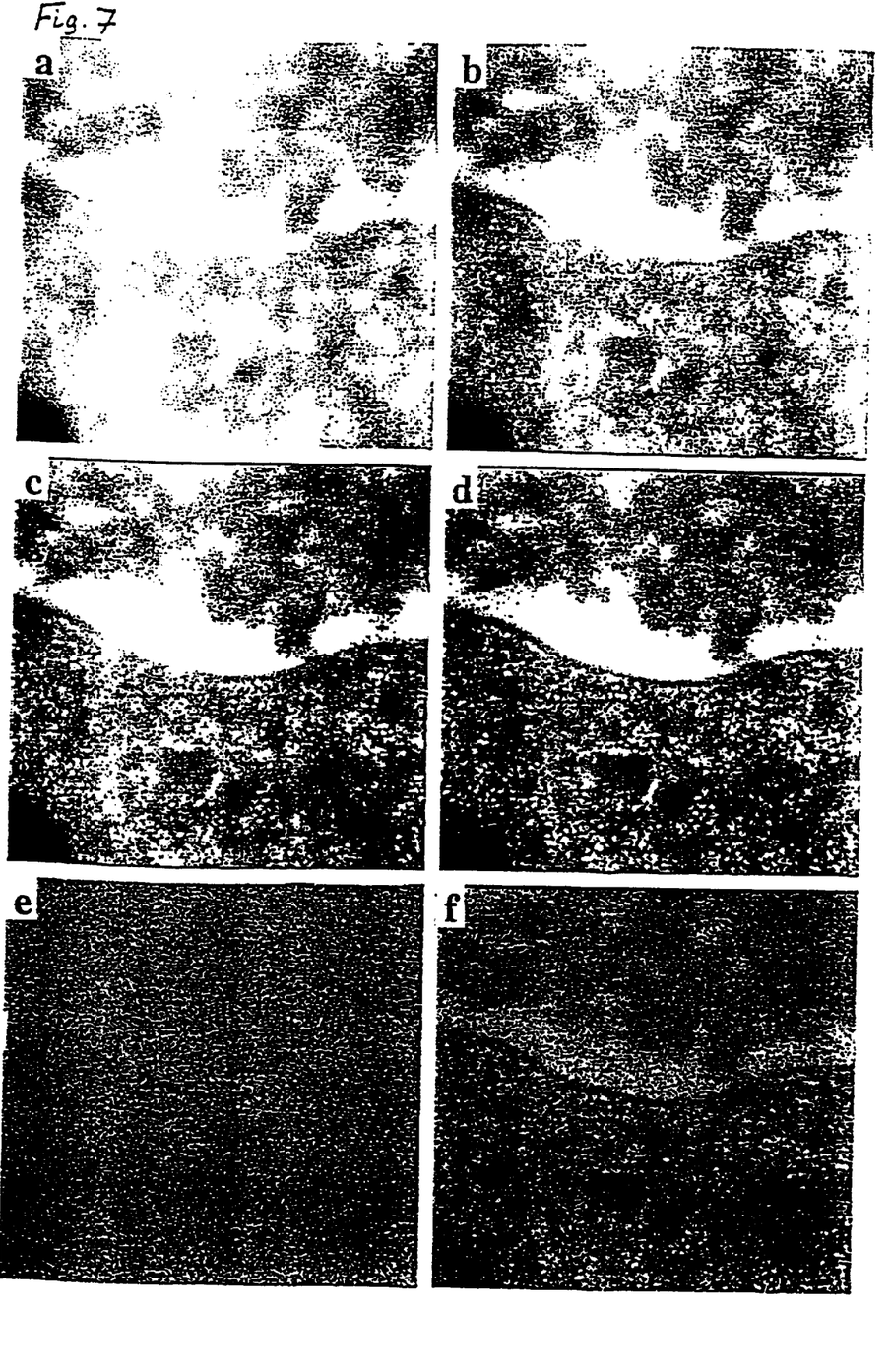
FIG. 7 shows images at 50, 80, 115 and 150 eV (FIGS. 7a to 7d) a negative test (FIG. 7e) and an image of the element-specific intensities (FIG. 7f).

In contrast to the specimen model described previously, the image on the phosphorus edge was taken at 150 rather than 160 eV. Since the phosphorus edge displays a broad maximum, this causes virtually no difference.

A background function with the formula shown below was calculated as a negative result, as a function of the intensities at 50 and 80 eV:

$$I_{U,115} = a + \sum_{i=1}^{N=2} b_i I_{50}^i + \sum_{i=1}^{N=2} c_i I_{80}^i$$

For each pixel, the intensity of the sample images at 50 and 80 eV was inserted into this function and the background was determined at 115 eV. The result in FIG. 7 shows practically no signal other than noise. This shows that the reference sample describes the contrast in the preparation well.

Additionally, in order to detect the phosphorus in the preparation, the function for the background was calculated at 150 eV, i.e. the phosphorus edge, with the aid of the reference sample. This background was subtracted from the image of the sample at 150 eV, and the phosphorus distribution was measured using the formula:

$$I_{E,150} = I_{2'p} - \left( a + \sum_{i=1}^{N=2} b_i I_{80}^i + \sum_{i=1}^{N=2} c_i I_{115}^i \right)$$

(see FIG. 7f).

The reference sample does not have to be recorded separately. Rather, it is possible to prepare the reference sample either on the same carrier as the preparation or to measure an area of the preparation as a reference sample that is guaranteed not to contain the sought element.

Accordingly, while only a few embodiments of the present invention have been shown and described, it is obvious that many changes and modifications may be made thereunto without departing from the spirit and scope of the invention.

What is claimed is:

1. a procedure for the detection of an element in a sample comprising the steps of:

measuring a first image of intensities $I_{1p}$ of the sample for an energy loss before an element edge using a transmission electronic microscope;

measuring a second image of intensities $I_{2'p}$ for an energy loss in the area of the element edge;

determining non-element-specific intensities $I_1$ of the sample for an energy loss before the element specific signal edge for various points at a reference sample point that does not contain the element;

determining non-element-specific intensities $I_2$ for and energy loss in the area of the element specific signal edge;

calculating an approximation function $I_2(I_1)$;

calculating an image of element-specific intensities $I_E$ from these values by calculating the corresponding intensity $I_{2p}$ with approximation function for every point in the first image with the intensity $I_{1P}$ and by determining the difference between the measured intensity $I_{2'p}$ and and the calculated intensity $I_{2p}$ as the element-specific intensity $I_E$ for the corresponding point in the second image.

2. A procedure according to claim 1, wherein the reference sample displays a configuration with different sample thicknesses.

3. A procedure according to claim 2, wherein the configuration has the form of a ramp.

4. A procedure according to claim 1, wherein the reference sample displays at least the thickness of the sample.

5. A procedure according to claim 1, wherein the reference sample contains the main component of the sample.

6. A procedure according to claim 1, wherein the reference sample consists of pure carbon or silicon.

7. A procedure according to claim 1, where in the intensity of each point is replaced with a mean value of its environment to calculate the corresponding intensity $I_{2p}$.

8. A procedure according to claim 1, wherein the quality of the approximation function $I_2$ is determined by means of statistical functions.

9. A procedure according to claim 1, wherein the detected material is the element phosphorus.

10. A procedure according to claim 1, further comprising the steps of:

measuring at least a third image of intensities $I_{3p}$ for a third energy loss, lying before the element specific signal edge, and differing from the energy loss of the first image;

calculating third intensities $I_1$, $I_3$;

calculating the image of the element-specific intensities $I_E$, by calculating the corresponding intensity $I_{2p}$ with the approximation function for every point in the first and third image; and determining the difference between the measured intensity $I_{2'p}$ and the calculated intensity $I_{2p}$ as the element-specific intensity $I_E$ for the corresponding point in the second image.

* * * * *

UNITED STATES PATENT AND TRADEMARK OFFICE
CERTIFICATE OF CORRECTION

PATENT NO.    : 6,586,735 B1
DATED         : July 1, 2003
INVENTOR(S)   : Haking et al.

It is certified that error appears in the above-identified patent and that said Letters Patent is hereby corrected as shown below:

<u>Title page,</u>
Item [30], Foreign Application Priority Data, should correctly read:

-- [30]          Foreign Application Priority Data
        July 4, 1997     (DE) ------------------------197 28 698
        March 16, 1998  (DE) -----------------------198 11 395.1 --

Signed and Sealed this

Twentieth Day of January, 2004

JON W. DUDAS
*Acting Director of the United States Patent and Trademark Office*